United States Patent
Wei et al.

(10) Patent No.: US 10,454,124 B2
(45) Date of Patent: Oct. 22, 2019

(54) HIGHLY STABLE PHENAZINE DERIVATIVES FOR AQUEOUS REDOX FLOW BATTERIES

(71) Applicant: Battelle Memorial Institute, Richland, WA (US)

(72) Inventors: Xiaoliang Wei, Richland, WA (US); Wei Wang, Richland, WA (US); Aaron M. Hollas, Pasco, WA (US); Vincent L. Sprenkle, Richland, WA (US); Zimin Nie, Richland, WA (US); Bin Li, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 49 days.

(21) Appl. No.: 15/625,750

(22) Filed: Jun. 16, 2017

(65) Prior Publication Data

US 2018/0366757 A1    Dec. 20, 2018

(51) Int. Cl.
| | |
|---|---|
| *H01M 8/18* | (2006.01) |
| *H01M 4/90* | (2006.01) |
| *C07D 241/46* | (2006.01) |
| *H01M 8/08* | (2016.01) |
| *H01M 4/96* | (2006.01) |

(52) U.S. Cl.
CPC .......... *H01M 8/188* (2013.01); *C07D 241/46* (2013.01); *H01M 4/90* (2013.01); *H01M 4/9016* (2013.01); *H01M 4/96* (2013.01); *H01M 8/08* (2013.01); *H01M 2300/0002* (2013.01)

(58) Field of Classification Search
CPC .......... H01M 8/188; H01M 8/08; H01M 4/90; H01M 4/9016; H01M 2300/0002; C07D 241/46

USPC ........................................................ 429/231.2
See application file for complete search history.

(56) References Cited

U.S. PATENT DOCUMENTS

| | | | | |
|---|---|---|---|---|
| 9,614,245 | B2* | 4/2017 | Narayan | H01M 8/188 |
| 2013/0224538 | A1* | 8/2013 | Jansen | H01M 8/188 |
| | | | | 429/72 |
| 2014/0370405 | A1* | 12/2014 | Zhang | H01M 8/20 |
| | | | | 429/418 |

(Continued)

FOREIGN PATENT DOCUMENTS

| | | |
|---|---|---|
| JP | 2003-338318 | 11/2003 |
| JP | 2003338318 A | * 11/2003 |

(Continued)

OTHER PUBLICATIONS

Machine translation of JP 2003-338318 (no date).*

(Continued)

*Primary Examiner* — Amanda C. Walke
(74) *Attorney, Agent, or Firm* — Klarquist Sparkman, LLP

(57) ABSTRACT

Embodiments of an aqueous electrolyte comprising a base and a phenazine derivative are disclosed. Redox flow batteries including the aqueous electrolyte are also disclosed. The phenazine derivative has a chemical structure according to formula I:

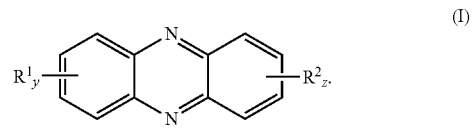

(I)

20 Claims, 6 Drawing Sheets

(56) References Cited

U.S. PATENT DOCUMENTS

2015/0236543 A1    8/2015   Brushett et al.
2017/0162916 A1*   6/2017   Guarr ................ H01M 10/0525

FOREIGN PATENT DOCUMENTS

| JP | 2015018717 A * | 1/2015 |
| WO | WO 2014-204985 A1 | 6/2014 |
| WO | WO 2016/011393 A1 | 1/2016 |
| WO | WO 2016/024919 A1 | 2/2016 |

OTHER PUBLICATIONS

Winsberg, et al., "TEMPO/Phenazine Combi-Molecule: a Redox-Active Material for Symmetric Aqueous Redox-Flow Batteries," *ACS Energy Letters*, Oct. 17, 2016, 1:976-980.

International Search Report and Written Opinion dated Oct. 5, 2018, for PCT Patent Application No. PCT/US2018/037246, 10 pp.

Michida, T. et al., "Electrochemical and ESR spectroscopic study of 2,7-disubstituted phenazines," *Chemical and Pharmaceutical Bulletin* 1996, vol. 44, No. 8, pp. 1448-1453.

\* cited by examiner

HIGHLY STABLE PHENAZINE DERIVATIVES FOR AQUEOUS REDOX FLOW BATTERIES

ACKNOWLEDGMENT OF GOVERNMENT SUPPORT

This invention was made with Government support under Contract DE-AC05-76RL01830 awarded by the U.S. Department of Energy. The Government has certain rights in the invention.

FIELD

This invention discloses embodiments of an aqueous electrolyte comprising a phenazine derivative. This invention also concerns embodiments of redox flow battery systems including the disclosed aqueous electrolyte.

BACKGROUND

The pursuit of low-cost, grid scale battery storage systems has been spurred by the inherent intermittency issues related to renewable energy generation, i.e. solar and wind, and their increasing integration into the power grid. Interest in these systems has also stemmed from their potential to stabilize the grid by balancing peak load during times of high energy demand. The use of redox-flow batteries (RFB) has gained increased attention for these applications. The most attractive feature of these systems relative to traditional lithium ion batteries is their ready scalability: within a RFB, electrolyte materials are dissolved in solution, maintained in a storage vessel, and pumped to the cell compartments.

A RFB stores electrical energy in reduced and oxidized species dissolved in two separate electrolyte solutions, the anolyte and the catholyte. The anolyte and the catholyte circulate through a cell electrode separated by a membrane or separator. Redox flow batteries are advantageous for energy storage because they are capable of tolerating fluctuating power supplies, repetitive charge/discharge cycles at maximum rates, overcharging, overdischarging, and/or because cycling can be initiated at any state of charge.

While the most widely studied and current state-of-the-art systems are based on vanadium redox-flow batteries, the high cost of vanadium has prevented their wide scale distribution. The use of low-cost, water-soluble, organic charge carriers has emerged as a promising alternative to vanadium-based systems. Existing aqueous systems suffer from poor solubility of the charge carriers, side reactions, low cell voltages, instability, and/or capacity fade.

SUMMARY

Embodiments of aqueous electrolytes comprising phenazine derivatives are disclosed. Electrolyte systems and redox flow battery systems including an anolyte comprising a phenazine derivative are also disclosed.

An aqueous electrolyte includes a phenazine derivative according to formula I or a salt thereof, where formula I is

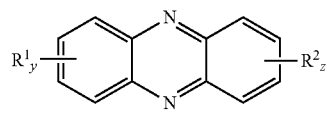

(I)

wherein $R^1$ and $R^2$ independently are —H, —$R^aOR^3$, —$R^aSO_3H$, —$R^aCOOH$, —$R^aSO_3M$, —$R^aCOOM$, —$R^aNR^3_3X$, —$R^aNR^3_2$, —$R^aPO(OH)_2$, —$R^aSH$, —$R^aPS(OH)_2$, —$R^a$—O—PO(OH)$_2$, —$R^a$—O—PS(OH)$_2$, —$R^a$—S—PS(OH)$_2$, or —(OCH$_2$CH$_2$)$_n$OR$^3$, wherein at least one $R^1$ or $R^2$ is other than hydrogen; each $R^3$ independently is H or $C_1$-$C_5$ alkyl; each $R^a$ independently is absent or $C_1$-$C_5$ alkyl; M is a cation; X is an anion; n is an integer $\geq 1$; and y+z=1, 2, 3, 4, 5, 6, 7, or 8, where y and z independently are 0, 1, 2, 3, or 4. In some embodiments, the phenazine derivative is present in the electrolyte at a concentration within a range of from 0.01 M to 8 M.

In any or all of the above embodiments, the aqueous electrolyte may further comprise an acid or a base. In one embodiments, the aqueous electrolyte consists essentially of a base, the phenazine derivative, and water. In an independent embodiment, the aqueous electrolyte consists essentially of an acid, the phenazine derivative, and water. In certain embodiments, the aqueous electrolyte is neutral or substantially neutral (has an average pH within a range of 6.5 to 7.5), and the electrolyte further comprises at least one aqueous-soluble neutral salt.

In any or all of the above embodiments, y may be 0, 1, or 2; z may be 1 or 2, and y+z=2, 3, or 4. In any or all of the above embodiments, each $R^1$ independently may be —OH, —SO$_3$H, —COOH, —OCH$_3$, or —CH$_2$N(CH$_3$)$_3$X; and each $R^2$ independently may be —OH, —SO$_3$M, or —CH$_2$N(CH$_3$)$_3$X.

In any or all of the above embodiments, the phenazine derivative may have a structure according to formula II

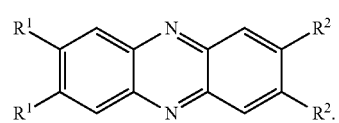

(II)

In some embodiments, the phenazine derivative has a structure according to formula II, and each $R^1$ and $R^2$ independently is —H, —OH, —SO$_3$H, —COOH, —OCH$_3$, —SO$_3$M, or —CH$_2$N(CH$_3$)$_3$X. In certain embodiments, each $R^1$ independently is —H, —OH, —SO$_3$H, —COOH, —OCH$_3$, or —CH$_2$N(CH$_3$)$_3$X; and each $R^2$ independently is —H, —OH, —SO$_3$M, or —CH$_2$N(CH$_3$)$_3$X.

Exemplary phenazine derivatives include

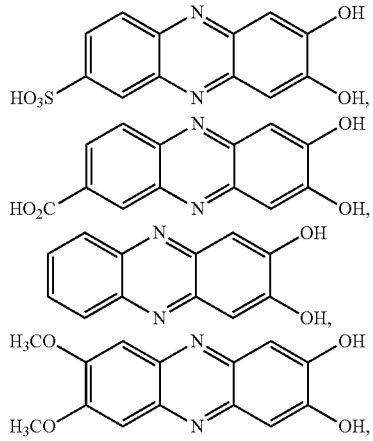

-continued

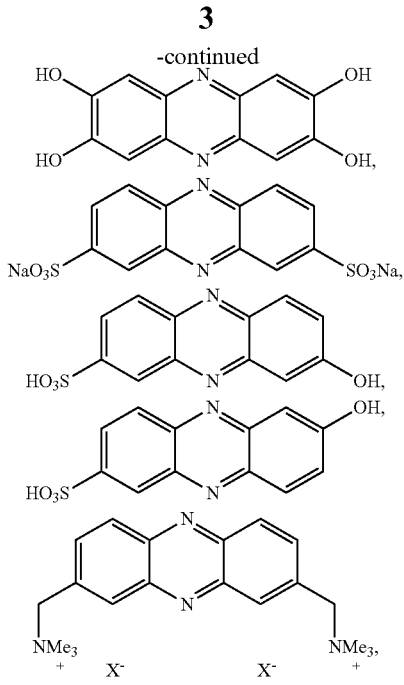

or any combination thereof. In certain embodiments, the phenazine derivative is:

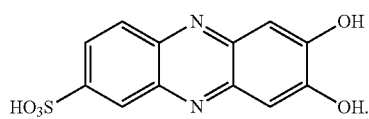

Some embodiments of an aqueous electrolyte system for use in a redox flow battery system comprise an aqueous anolyte comprising the aqueous electrolyte described above, and an aqueous catholyte comprising an electrochemically active material. In some embodiments, the aqueous catholyte further comprises a base or an acid. In any or all of the above embodiments, the electrochemically active material of the aqueous catholyte may comprise $K_4Fe(CN)_6$, $K_3Fe(CN)_6$, or a combination thereof.

In some embodiments, the aqueous anolyte comprises an alkali metal base and

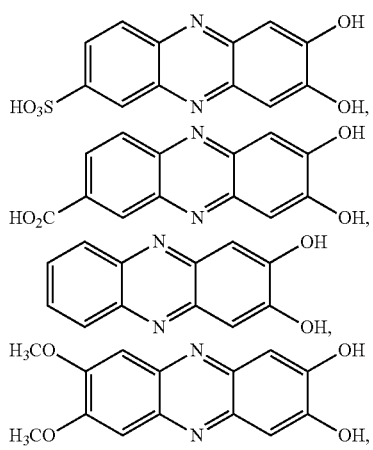

-continued

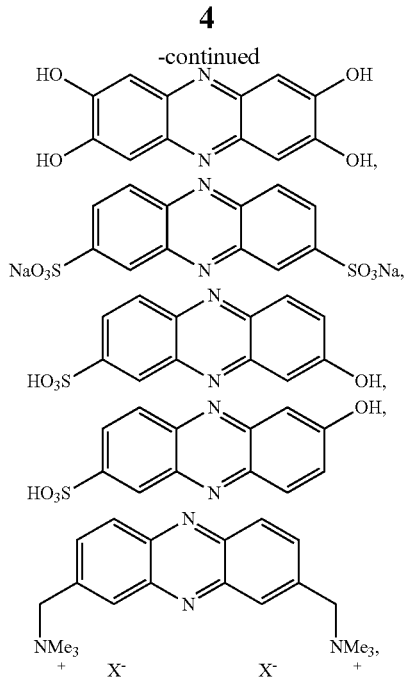

or any combination thereof; and the aqueous catholyte comprises an alkali metal base and $K_4Fe(CN)_6$. In certain embodiments, the aqueous anolyte comprises an alkali metal base and

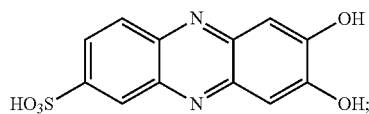

and the aqueous catholyte comprises the alkali metal base and $K_4Fe(CN)_6$, $K_3Fe(CN)_6$, or a combination thereof.

Some embodiments of a redox flow battery system comprise an aqueous electrolyte system as described above and a separator. The redox flow battery system may further comprise a carbon-based anode and a carbon-based cathode.

The foregoing and other objects, features, and advantages of the invention will become more apparent from the following detailed description, which proceeds with reference to the accompanying figures.

DETAILED DESCRIPTION

Figure 1:
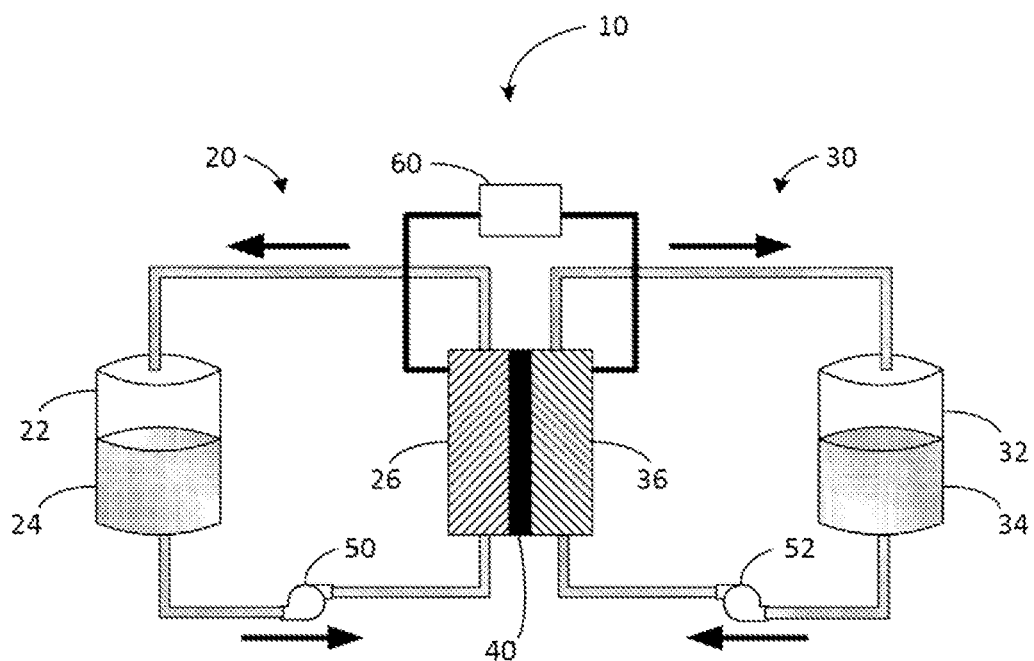
FIG. 1 is a schematic diagram of an exemplary redox flow battery system.

Embodiments of aqueous electrolytes comprising phenazine derivatives are disclosed. Certain embodiments of the aqueous electrolytes are useful as anolytes in aqueous redox flow batteries. Advantageously, some embodiments of the phenazine derivatives undergo 2e$^-$ oxidation/reduction. Embodiments of an aqueous RFB system also are disclosed.

I. Definitions and Abbreviations

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly indicates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods, as known to those persons of ordinary skill in the art. When directly and explicitly distinguishing embodiments from discussed prior art, the embodiment numbers are not approximates unless the word "about" is recited.

In order to facilitate review of the various embodiments of the disclosure, the following explanations of specific terms are provided:

Alkyl: A hydrocarbon group having a saturated carbon chain. The chain may be cyclic, branched or unbranched. The term lower alkyl means the chain includes 1-10 carbon atoms. Unless expressly referred to as an "unsubstituted alkyl," an alkyl group can either be unsubstituted or substituted.

Amino: A chemical functional group —N(R)R' where R and R' are independently hydrogen, alkyl, heteroalkyl, haloalkyl, aliphatic, heteroaliphatic, aryl (such as optionally substituted phenyl or benzyl), heteroaryl, alkylsulfano, or other functionality. A "primary amino" group is —NH$_2$. "Mono-substituted amino" means a radical —N(H)R substituted as above and includes, e.g., methylamino, (1-methylethyl)amino, phenylamino, and the like. "Di-substituted amino" means a radical —N(R)R' substituted as above and includes, e.g., dimethylamino, methylethylamino, di(1-methylethyl)amino, and the like. A quaternary amino group has the formula —N(R)R'R"$^+$ where R, R' and R" are independently hydrogen, alkyl, heteroalkyl, haloalkyl, aliphatic, heteroaliphatic, aryl (such as optionally substituted phenyl or benzyl), heteroaryl, alkylsulfano, or other functionality.

Capacity: The capacity of a battery is the amount of electrical charge a battery can store (charge capacity) and deliver (discharge capacity). The discharge capacity is typically expressed in units of mAh, or Ah, and indicates the charge a battery can produce over a period of one hour. The term capacity fade refers to a decrease in the charge/discharge capacity over time and result in shorter charge/discharge cycles when the current/voltage is held constant.

Carboxyl: A chemical functional group with the formula —COON. Substituted carboxyl refers to —COOR where R is aliphatic, heteroaliphatic, alkyl, or heteroalkyl.

Cell: As used herein, a cell refers to an electrochemical device used for generating a voltage or current from a chemical reaction, or the reverse in which a chemical reaction is induced by a current. Examples include voltaic cells, electrolytic cells, redox flow cells, and fuel cells, among others. Multiple single cells can form a cell assembly, often termed a stack. A battery includes one or more cells, or even one or more stacks.

Coulombic efficiency (CE): The efficiency with which charges are transferred in a system facilitating an electrochemical reaction. CE may be defined as the amount of charge exiting the battery during the discharge cycle divided by the amount of charge entering the battery during the charging cycle.

Electrochemically active component: A component (an element, an ion, or a compound) that is capable of forming redox pairs having different oxidation and reduction states, e.g., ionic species with differing oxidation states, a metal cation and its corresponding neutral metal atom, or a metal cation and its corresponding metal ions at a different oxidation state. In a flow battery, an electrochemically active component refers to the chemical species that participate in the redox reaction during the charge and discharge processes, significantly contributing to the energy conversions that ultimately enable the battery to deliver/store energy. By "significantly contributing" is meant that a redox pair including the electrochemically active component contributes at least 10% of the energy conversions that ultimately enable the battery to deliver/store energy. In some embodiments, the redox pair including the electrochemically active component contributes at least 50%, at least 75%, at least 90%, or at least 95% of the energy conversions in a catholyte or anolyte comprising the electrochemically active component.

Electrolyte: A substance containing free ions and/or radicals that behaves as an ionically conductive medium. In a redox flow battery, some of the free ions and/or radicals are electrochemically active components. An electrolyte in contact with the anode, or negative half-cell, may be referred to as an anolyte, and an electrolyte in contact with the cathode, or positive half-cell, may be referred to as a catholyte. The anolyte and catholyte are often referred to as the negative electrolyte and positive electrolyte, respectively, and these terms can be used interchangeably. As used herein, the terms anolyte and catholyte refer to electrolytes composed of electrochemically active components and an aqueous supporting solution.

Energy efficiency (EE): The product of coulombic efficiency and voltage efficiency. EE=CE×VE.

Redox pair or redox couple: An electrochemically active component and its corresponding oxidized (or reduced) component. Exemplary redox pairs include, but are not limited to, $[Fe(CN)_6]^{4-}/[Fe(CN)_6]^{3-}$, Li+/Li, etc.

Substituted: A fundamental compound, such as an aryl or aliphatic compound, or a radical thereof, having coupled thereto one or more substituents, each substituent typically replacing a hydrogen atom on the fundamental compound. Exemplary substituents include, but are not limited to, aliphatic (alkyl, alkenyl, or alkynyl), heteroalkyl, alkoxy, alkylaryl (e.g., $H_3C-C_6H_4-$), alkylthio, amino, amide, aryl, heteroaryl, arylalkyl (e.g., $C_6H_5CH_2-$), acyl (R—C (O)—), hydroxyl, thiol, thioalkoxy, alkylamino, aminoalkyl, or other organic functionality. Each substituent may be further substituted, e.g., haloaliphatic, haloalkoxy, haloaryl, aminoaliphatic, aminoaryl, etc.

Voltage efficiency (VE): The voltage produced by the battery while discharging divided by the charging voltage.

II. Electrolytes Comprising a Phenazine Derivative

Phenazine advantageously undergoes a 2e⁻ redox reaction (Equation 1), thereby increasing the energy per unit of redox material and/or the storage capacity of a battery. However, phenazine is insoluble in water due to the hydrophobic conjugated aromatic rings, rendering it unsuitable for use in aqueous electrolytes.

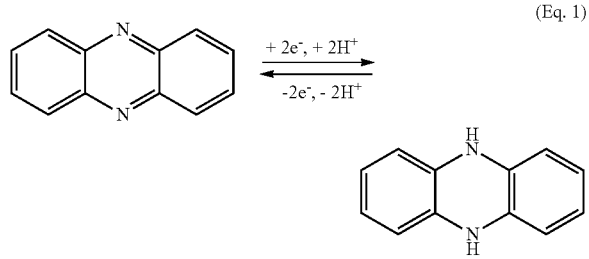

(Eq. 1)

Embodiments of aqueous electrolytes comprising a phenazine derivative are disclosed. In some embodiments, the phenazine derivative includes one or more substituents that increase aqueous solubility, alter pH-dependent solubility, are capable of undergoing deprotonation, and/or improve electrolyte stability. The phenazine derivative may, for example, include substituents that provide negatively charged species in basic solutions, increase solubility, and/or resist cell crossover with common cation-exchange membranes. In certain embodiments, the phenazine derivative also has a negatively shifted redox potential compared to phenazine. Without wishing to be bound by a particular theory of operation, the negatively shifted redox potential may be attributed to the pH-dependent nature of proton-coupled electron transfer (POET) reactions involving the phenazine derivative, and/or electron-donating moieties, such as hydroxy groups. In some embodiments, the redox potential is as low as −1 V vs. Ag/AgCl in basic electrolytes. Some embodiments of the disclosed phenazine derivatives are low-cost, long-lasting, and/or high voltage species amenable to aqueous redox flow batteries operating at high pH.

The phenazine derivative is a compound according to formula I:

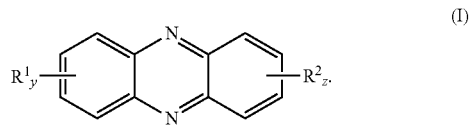

(I)

wherein $R^1$ and $R^2$ independently are —H, —$R^aOR^3$, —$R^aSO_3H$, —$R^aCOOH$, —$R^aSO_3M$, —$R^aCOOM$, —$R^aNR^3_3X$, —$R^aNR^3_2$, —$R^aPO(OH)_2$, —$R^aSH$, —$R^aPS(OH)_2$, —$R^a$—O—$PO(OH)_2$, —$R^a$—O—$PS(OH)_2$, —$R^a$—S—$PS(OH)_2$, or —$(OCH_2CH_2)_nOR^3$ wherein at least one $R^1$ or $R^2$ is other than hydrogen; each $R^3$ independently is H or $C_1$-$C_5$ alkyl; each $R^a$ independently is absent or $C_1$-$C_5$ alkyl; M is a cation; X is an anion; n is an integer ≥1; and y+z=1, 2, 3, 4, 5, 6, 7, or 8, where y and z independently are 0, 1, 2, 3, or 4. In some embodiments, n is an integer from 1 to 100, such as an integer from 1 to 75, from 1 to 50, from 1 to 25, or from 1 to 10. In some nonlimiting examples, n is 1, 2, 3, 4, 5, 6, 7, 8, 9, 10, 11, 12, 13, 14, 15, 16, 17, 18, 19, 20, 21, 22, 23, 24, or 25.

M is a cation. In some embodiments, M is a +1 cation, such as a +1 metal ion (e.g., an alkali metal ion), ammonium $(NR'_4)^+$, iminium $(R'_2C=NR'_2)^+$, phosphonium $(PR'_4)^+$, sulfonium $(SR'_3)^+$, or an organic cation with a +1 charge, such as pyridinium, pyrrolidinium, imidazolium, piperidinium, pyrazolium, thiazolium, anilinium, benzylammonium, or 2-phenylethylammonium, among others. Each R' independently is hydrogen or lower ($C_1$-$C_{10}$) alkyl. Each of the organic cations can be substituted or unsubstituted unless otherwise specified. In certain embodiments, M is an alkali metal ion, such as Na⁺ or K⁺. In an independent embodiment, M is a +2 cation, such as an alkaline earth metal or transition metal cation. Exemplary +2 cations include, but are not limited to $Mg^{2+}$ and $Zn^{2+}$.

X is an anion. In some embodiments, X is a −1 anion, such as halide, hydroxide, thiol, nitrate, nitrite, acetate, formate, hydrogen sulfate, dihydrogen phosphate, hydrogen carbonate, amide, cyanide, cyanate, thiocyanate, or ferrocyanate. In certain embodiments, X is a halide.

The phenazine derivative has at least one $R^1$ or $R^2$, such that y+z=1, 2, 3, 4, 5, 6, 7, or 8. In one embodiment, y+z=1, 2, 3, 4, 5, or 6. In an independent embodiment, y+z=2, 3, or 4. In certain embodiments, y is 0, 1, or 2, z is 1 or 2, and y+z=2, 3, or 4. In one embodiment, y is 1 or 2, and z is 1 or 2. In an independent embodiment, y is 1 and z is 1. In another independent embodiment, y is 1 and z is 2. In still another independent embodiment, y is 2 and z is 2. In yet another independent embodiment, y is 0 and z is 2.

In some embodiments, each $R^1$ and $R^2$ independently is —OH, —$SO_3H$, —$SO_3M$, —COOH, —$OCH_3$, or —$CH_2N(CH_3)_3X$. In certain embodiments, each $R^1$ independently is —OH, —$SO_3H$, —COOH, —$OCH_3$, or —$CH_2N(CH_3)_3X$; and each $R^2$ independently is —OH, —$SO_3M$, or —$CH_2N(CH_3)_3X$.

In some embodiments, the phenazine derivative has a structure according to formula II:

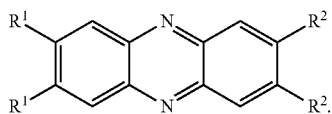

where $R^1$ and $R^2$ are as previously described for formula I. In certain embodiments, when the phenazine derivative has a structure according to formula II, each $R^1$ and $R^2$ independently is —H, —OH, —SO$_3$H, —COOH, —OCH$_3$, —SO$_3$M, or —CH$_2$N(CH$_3$)$_3$X. In certain embodiments, when the phenazine derivative has a structure according to formula II, each $R^1$ independently is —H, —OH, —SO$_3$H, —COOH, —OCH$_3$, or —CH$_2$N(CH$_3$)$_3$X; and each $R^2$ independently is —H, —OH, —SO$_3$M, or —CH$_2$N(CH$_3$)$_3$X.

Exemplary phenazine derivatives include, but are not limited to, the following compounds and salts thereof:

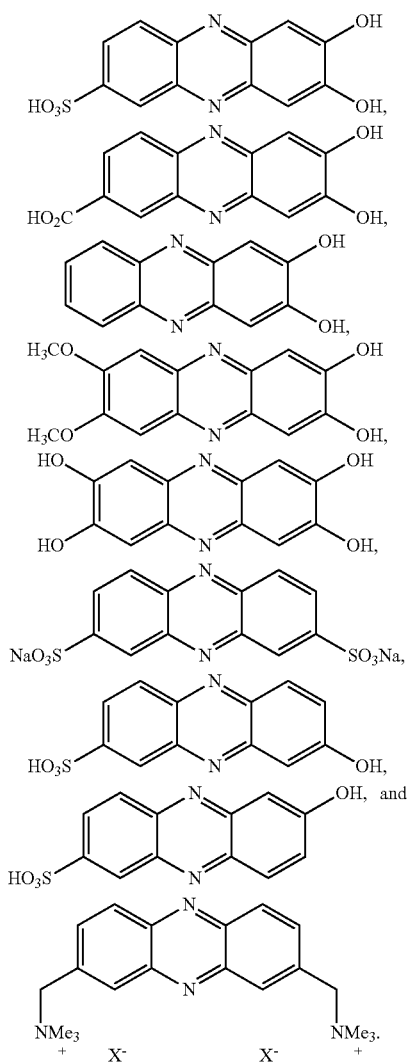

In one embodiment, an aqueous electrolyte comprises a base and a phenazine derivative as disclosed herein. In an independent embodiment, an aqueous electrolyte comprises an acid and a phenazine derivative as disclosed herein. In certain embodiments, the aqueous electrolyte does not include any electrochemically active component other than the phenazine derivative.

The aqueous electrolyte may consist essentially of, or consist of, the base or the acid, the phenazine derivative, and water. As used herein, "consists essentially of" means that the electrolyte includes no other components that materially affect battery performance. In particular, "consists essentially of" means that the electrolyte does not include any electrochemically active component other than the phenazine derivative. The electrolyte may include components that do not materially affect battery performance during charging and/or discharging, for example, non-electrochemically active species such as alkali metal cations. In some embodiments, the electrolyte is devoid of, or substantially devoid of (contains less than 2 wt % or less than 2 vol %), of an organic solvent. In certain embodiments, the electrolyte is devoid of an organic solvent.

Some embodiments of the disclosed aqueous electrolytes include a base. Suitable bases include water-soluble metal hydroxides (e.g., alkali metal hydroxides), ammonium hydroxide, or mixtures thereof. In certain examples, the base is NaOH. In some embodiments, the base concentration in the electrolyte is within a range of 0.05 M to 5 M, such as within a range of 0.1 M to 5 M, 0.5 M to 3 M, 0.5 M to 2 M, or 0.5 M to 1.5 M.

Some embodiments of the disclosed aqueous electrolytes include an acid. Suitable acids include, but are not limited to, binary acids (e.g., HCl, HBr, HI), sulfuric acid, nitric acid, phosphoric acid, and combinations thereof. In some embodiments, the acid concentration in the electrolyte is within a range of 0.05 M to 5 M, such as within a range of 0.1 M to 5 M, 0.5 M to 3 M, 0.5 M to 2 M, or 0.5 M to 1.5 M.

Some embodiments of the disclosed aqueous electrolyte include neither a base nor an acid; instead, the aqueous electrolyte is neutral (i.e., has an average pH of 7) or substantially neutral (i.e., has an average pH within a range of 6.5 to 7.5, such as an average pH within a range of 6.8 to 7.2 or 6.9 to 7.1). An average pH is determined by measuring the pH of the electrolyte a plurality of times and determining the mathematical average. The neutral electrolyte may include at least one aqueous-soluble neutral salt other than a phenazine derivative salt, such as, for example, a halide, sulfate, or nitrate salt, or any combination thereof. An aqueous soluble neutral salt has a solubility in water of at least 0.1 M at ambient temperature, and the electrolyte comprising the neutral salt is substantially neutral as defined above. In certain embodiments, the salt is an alkali metal salt. Exemplary salts include, but are not limited to, aqueous-soluble sodium and potassium salts such as NaCl, KCl, Na$_2$SO$_4$, K$_2$SO$_4$, and combinations thereof. In certain embodiments, the electrolyte consists essentially of, or consists of, the neutral salt, the phenazine derivative, and water.

In some embodiments, the concentration of the phenazine derivative in the electrolyte is within a range of from 0.01 M up to the solubility limit of the phenazine derivative in the solution of water and base or water and acid, such as within a range of from 0.01 M to 8 M, 0.01 M to 6 M, 0.01 M to 4 M, 0.01 M to 3 M, 0.01 M to 2 M, 0.05 M to 2 M, 0.1 M to 1.5 M, 0.5 M to 1.5 M, 1 M to 8 M, 2 M to 8 M, 3 M to 8 M, or 4 M to 8 M. In one embodiment, the phenazine derivative is present in the electrolyte at a concentration within a range of 0.01 M to 4 M. In an independent embodiment, the phenazine derivative is present in the electrolyte at a concentration within a range of from 4 M to 8 M. Certain embodiments of the phenazine derivatives provide 2 moles of electron transfer per mole of the compound, thus providing, for example, 2 M electron transfer when the phenazine derivative concentration is 1 M. Remarkably, the solubility limit of 7,8-dihydroxy-phenazine-2-sulfonic acid (DHPS) reaches 1.45 M in 1 M NaOH, corresponding to 2.9 M transferred electrons.

Embodiments of the disclosed phenazine derivatives are N-proteo systems, i.e., the nitrogen atoms in the central ring are not substituted. This feature allows some embodiments of the disclosed phenazine derivatives to undergo proton-coupled electron transfer events upon electrochemical reduction/oxidation, whereby protonation/deprotonation events occur concomitantly with reduction/oxidation. These proton transfer events affect the thermodynamics of the second electron transfer, often resulting in a $2H^+/2e^-$ electrochemical event, i.e., the single step $2e^-$ transfer process shown in Eq. 1. The $2e^-$ process effectively increases the capacity of a cell including the electrolyte, and is a fundamental difference between the phenazine derivatives disclosed herein and other phenazine systems wherein the nitrogen atoms are alkylated. The electrochemical behavior exhibited by N-alkylated phenazines is fundamentally different with two discrete and separate $1e^-$ events, which limits the theoretical capacity.

The pH of the electrolyte is not a trivial issue; the pH dependence of proton-coupled electron transfer events, $$E = E^{o'} + \frac{0.059\,m}{n}\text{pH},$$

can have significant implications for the redox potential of redox-active organics, such as the disclosed phenazine derivatives, undergoing proton-coupled electron transfer events. In some embodiments, the use of high pH (basic) systems ensures a negative shift in redox potential for the anolyte material (phenazine) and/or increases the energy density of a cell including an embodiment of the disclosed electrolytes.

III. Phenazine Derivative Synthesis

Certain exemplary synthetic routes for making phenazine derivatives are shown below. A person of ordinary skill in the art will understand that a number of alternative synthetic methods exist for the formation of the phenazine core structure. Given the existence of multiple synthetic pathways and the various substituted precursors available, numerous phenazine derivatives can be prepared. Thus, the following methods are representative and do not indicate all available synthetic approaches.

Some embodiments of the disclosed phenazine derivatives are synthesized in a one-step process. For example, 7,8-dihydroxy-phenazine-2-sulfonic acid (DHPS) is synthesized in one step by refluxing a mixture of 3,4-diaminobenzene sulfonic acid and 2,5-dihydroxy-1,4-benzoquinone as shown in Scheme 1. The starting materials are readily available or can be easily synthesized from diaminobenzene and hydroquinone as shown below in Scheme 1.

Scheme 1

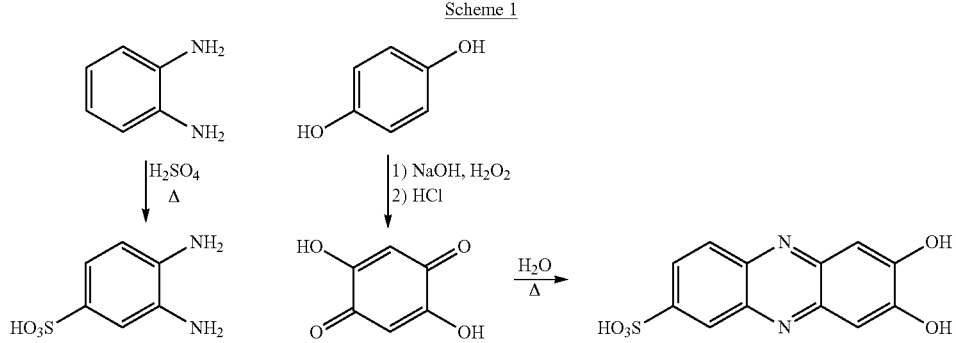

Diverse functionalization of the phenazine core is achieved through substitution of the phenylene diamine precursor and/or the quinone-based coupling partner. Functionalization modulates the redox properties and/or solubility of the phenazine derivative. A more generalized synthesis for derivatives prepared with 2,5-dihydroxy-1,4-benzoquinone and a substituted diaminobenzene, where $R^1$ and y are as previously described for general formula I, is shown in Scheme 2.

Scheme 2

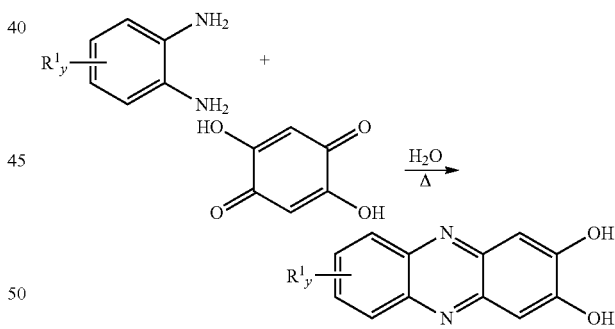

Derivatives with a single hydroxy group can be prepared from 1,4-benzoquinone as shown in Scheme 3.

Scheme 3

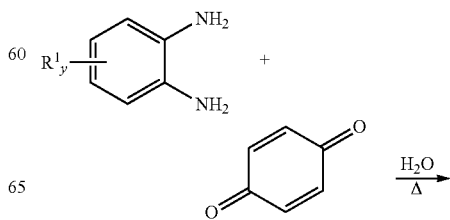

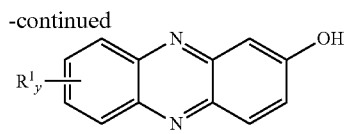

Another synthesis route utilizing substituted diphenylamines is shown in Scheme 4, wherein $R^1$, $R^2$, y, and z are as previously described for general formula I.

Scheme 4

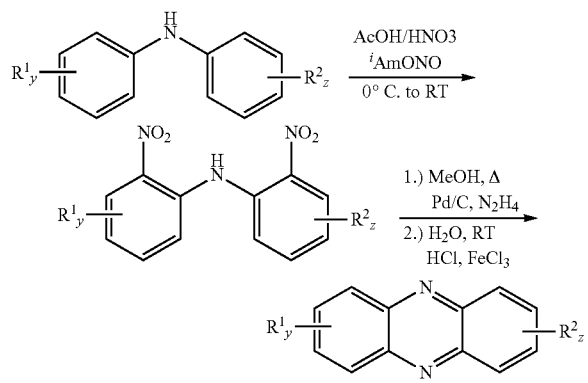

IV. Redox Flow Battery System

Redox flow batteries (RFBs) can provide electrical energy converted from chemical energy continuously, and are promising systems for energy storage to integrate renewable energies (e.g., solar and/or wind energy) into electrical supply grids. As shown in FIG. 1, some embodiments of a RFB system 10 comprise a positive half-cell 20 and a negative half-cell 30. The half-cells are separated by a membrane or separator 40, such as an ion-exchange membrane (cation- or anion-exchange membrane), ion conductive membrane (polymer or ceramic) or porous separator. The positive half-cell 20 comprises an electrode tank 22 containing a catholyte 24 and the negative half-cell 30 comprises an electrode tank 32 containing an anolyte 34. The anolyte and catholyte are solutions comprising electrochemically active components in different oxidation states. The electrochemically active components in the catholyte and anolyte couple as redox pairs. In some embodiments, at least one of the catholyte and anolyte redox active materials remains fully soluble during the charging and discharging cycles of the RFB.

During charging and discharging of the RFB, the catholyte and anolyte are continuously circulating via pumps 50, 52 through the positive and negative electrodes 26, 36, respectively, where redox reactions proceed, providing the conversion between chemical energy and electrical energy or vice-versa. To complete the circuit during use, positive and negative electrodes (including a current collector at each side) 26, 36 of the RFB system 10 are electrically connected through current collectors (not shown) with an external load 60. The electrodes are selected to be stable with the anolyte and catholyte. In some embodiments, the electrodes are carbon-based. Suitable carbon-based materials include, but are not limited to, carbon felt, carbon paper, and woven carbon cloth. Exemplary separators include, but are not limited to, cation-exchange membranes, such as Nafion™ N115, NR-212, and NR-211 membranes (available from Ion Power, Inc., New Castle, Del.).

Figure 2:
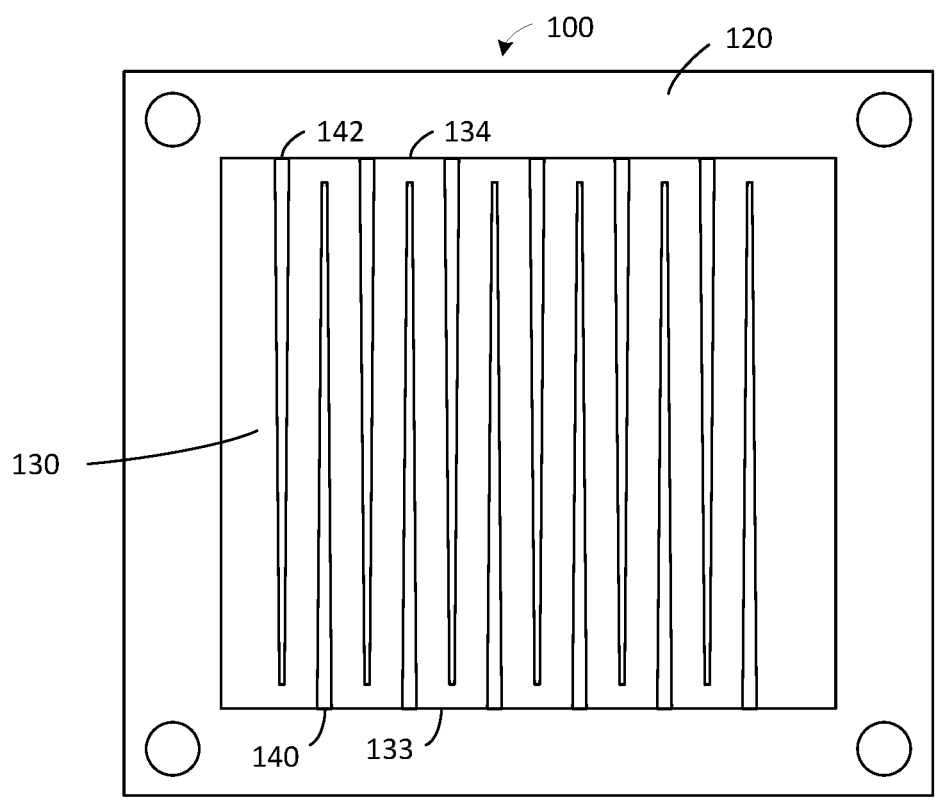
FIG. 2 is a simplified diagram of a flow half cell including interdigitated inlet and outlet flow channels.
Figure 3:
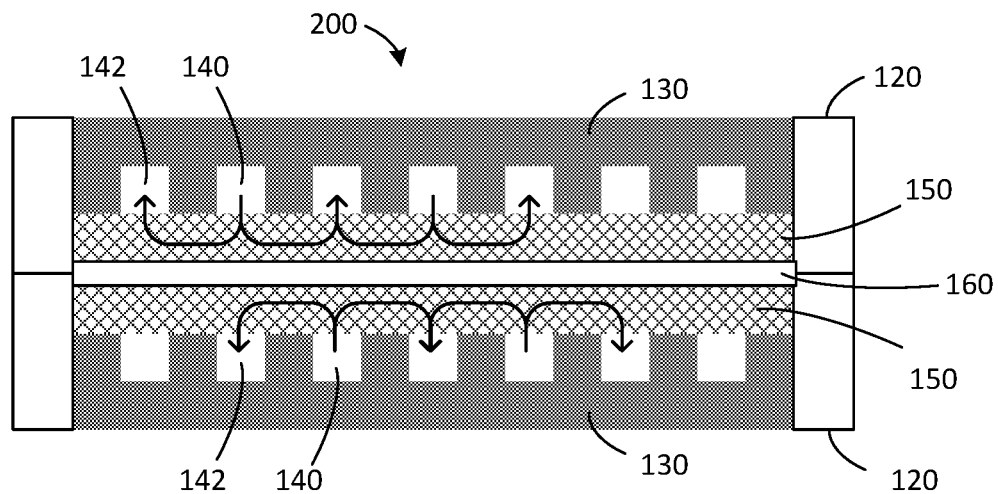
FIG. 3 is a cross-sectional view of an exemplary redox flow battery stack cell with an interdigitated design.

In some embodiments, the RFB is a flow cell with an interdigitated design of flow channels. FIG. 2 is a simplified diagram of one exemplary half cell 100 comprising a support frame 120 and a bipolar plate 130 with interdigitated inlet and outlet flow channels 140, 142. The inlet flow channels 140 extend inwardly from a first side edge 133 of the bipolar plate 130 and have a closed distal end. The outlet flow channels 142 extend inwardly from the opposing side edge 134 of the bipolar plate and also have a closed distal end. The bipolar plate 130 may also include flow channels on the opposing surface with anolyte circulating through the channels on one side of the plate and catholyte circulating through the flow channels on the opposing side. With reference to the cross-sectional view of FIG. 3, a redox flow battery stack cell 200 comprises two electrodes 150 and an ion-exchange membrane or separator 160. The electrodes 150 are disposed on either side of and in contact with the separator 160. The redox flow battery stack cell 200 further comprises two half cells 100 each half cell comprising a support frame 120 and bipolar plate 130. The half cells are positioned such that a bipolar plate 130 is in contact with each electrode 150. The electrode 150 may be porous so that an electrolyte may flow through the electrode. In some embodiments, the electrode 150 comprises a carbonaceous material, such as carbon felt, carbon paper, and woven carbon cloth. Exemplary separators include those described above. End plates on either side of the cell include a current collector in electrical communication with the cell (not shown). The arrows in FIG. 3 illustrate the direction of electrolyte flow through the redox flow battery stack cell 200. An electrolyte flowing through an inlet flow channel 140 cannot directly exit the inlet flow channel because the distal end of the inlet flow channel is closed (FIG. 2). As shown in FIG. 3, the electrolyte flows from the inlet flow channel 140 into the electrode 150, through the electrode 150 in a direction substantially perpendicular to the inlet flow channel 140, and subsequently into adjacent outlet flow distribution channels 142. Several cells may be assembled into a battery stack (not shown) with an end plate at each end of the stack.

Embodiments of the disclosed aqueous electrolytes comprising a phenazine derivative as disclosed herein are suitable for use as the anolyte. The catholyte is an aqueous solution comprising an electrochemically active material suitable for use in a redox flow battery. In one embodiment, the catholyte comprises a base and the electrochemically active material. In an independent embodiment, the catholyte comprises an acid and the electrochemically active material. The catholyte may consist essentially of, or consist of, water, the base or the acid, and the electrochemically active material. In certain embodiments, the base or acid is the same base acid, respectively, as that of the anolyte, and may have the same concentration as the base or acid in the anolyte. In some examples, the electrochemically active material in the catholyte is potassium ferrocyanide ($K_4Fe(CN)_6$). In certain examples, the catholyte is an aqueous solution comprising a base and $K_4Fe(CN)_6$. Because the phenazine derivatives undergo a $2e^-$ redox process, the amount (number of moles) of $K_4Fe(CN)_6$ in the catholyte in some embodiments is twice the amount of the phenazine derivative in the anolyte. In certain embodiments, coupling an anolyte comprising a phenazine derivative as disclosed herein with a catholyte comprising a ferrocyanide/ferricyanide redox pair yields an aqueous flow cell that exceeds the cell voltage of all other reported aqueous organic systems.

V. Examples

General Considerations: Reagents and solvents were used as received from commercial suppliers, 2,5-dihydroxy-1,4-benzoquinone was purchased from Sigma Aldrich and 3,4-diaminobenzenesulfonic acid was purchased from KareBay BioChem or synthesized according to published procedures.

Spectroscopic Methods: NMR spectra were obtained using a Varian Oxford 500 MHz spectrometer at 25° C.

Electrochemical Methods: Cyclic voltammetry experiments were performed with a CH Instruments model 660C potentiostat using a glassy carbon working electrode, a platinum wire counter electrode, and a Ag/AgCl reference electrode.

Flow Cell Tests: Graphite flow plates with an interdigitated design and a 10 cm$^2$ interface were used for flow cell testing (see, e.g., FIG. 2). The current collector on each side was comprised of a stacked layer of ELAT® carbon cloth (NuVant Systems Inc., Crown Point, Ind.) and CP-ESA carbon paper (SGL Carbon), and a layer of Nafion™ N115 membrane (available from Ion Power, Inc., New Castle, Del.) was employed as the separator. A Masterflex US peristaltic pump (Cole-Parmer, Vernon Hills, Ill.) was used to circulate the electrolytes through the electrodes at a flow rate of 60 mL min$^{-1}$. The flow cell was galvanostatically charged/discharged at room temperature on an Arbin BT-2000 battery tester (Arbin Instruments) in the voltage range of 1.5-1.0 V at current densities ranging from 20 to 100 mA/cm$^2$. Flow battery testing and electrolyte preparation was performed in a purge box under constant nitrogen flow. Anolyte and catholyte solutions were comprised of 50 mL of 1 M NaOH containing 0.1 M DHPS and 0.2 M $K_4Fe(CN)_6$, respectively. For 1M testing, the following changes were made: the current collector on each side was comprised of a stacked layer of Toyobo felt and CP-ESA carbon paper, the flow rate was increased to 100 mL/min, and charging/discharging was performed between 1.7-1.0 V. Electrolyte solutions were comprised of 1 M DHPS combined with 3 equiv. of NaOH, which was dissolved in 10 mL of 1 M NaOH, and 0.572 M $K_4Fe(CN)_6$ dissolved in 35 mL of 1 M NaOH.

EXAMPLE 1

Synthesis and Characterization of 7,8-dihydroxy-phenazine-2-sulfonic acid

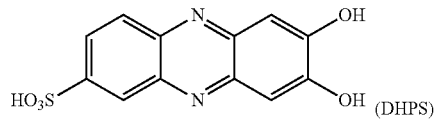
(DHPS)

7,8-dihydroxy-phenazine-2-sulfonic acid (DHPS) was synthesized in one step from refluxing a mixture of 3,4-diaminobenzene sulfonic acid and 2,5-dihydroxy-1,4-benzoquinone (see Scheme 1 supra). While both starting materials are available at modest prices from commercial suppliers, both are also derived in straightforward syntheses from the bulk commodity chemicals 1,2-phenylenediamine and 1,4-dihydroxybenzene, respectively, making the reported material scalable at low cost. A round bottomed flask was filled with 130 mL of water and began warming to 105° C. in an oil bath. While warming, solid 2,5-dihydroxy-1,4-benzoquinone (8.278 g., 0.059 mol) was added to the reaction flask. Then, over a 5 minute period, solid 3,4-diaminobenzenesulfonic acid (11.106 g., 0.059 mol) was added to the reaction mixture. After refluxing overnight the reaction mixture was cooled to room temperature, diluted with 150 mL of acetone, and then filtered to yield a gold solid which was washed with water and then acetone. The solid was dried under vacuum for 6 days to yield the product (17.063 g., 99%). $^1$H-NMR (500 MHz, DMSO-$d_6$) δ: 8.25 (s, 1H), 8.09 (d, J=8.5 Hz, 1H), 8.01 (d, J=8.5 Hz, 1H), 7.33 (s, 1H), 7.32 (s, 1H). The acidic proton could not be located due to exchange with residual water in the DMSO-$d_6$. $^{13}$C-NMR (125 MHz, DMSO-$d_6$): 156.2, 155.6, 148.8, 141.0, 140.1, 138.5, 137.0, 127.5, 126.8, 121.9, 106.0, 105.2. MS (ESI$^-$) m/z: 291 (M-H)$^-$. UV-vis (1 M NaOH) λ (ε/M$^{-1}$ cm$^{-1}$): 267 (48900), 297 (31800), 434 (23100).

Figure 4:
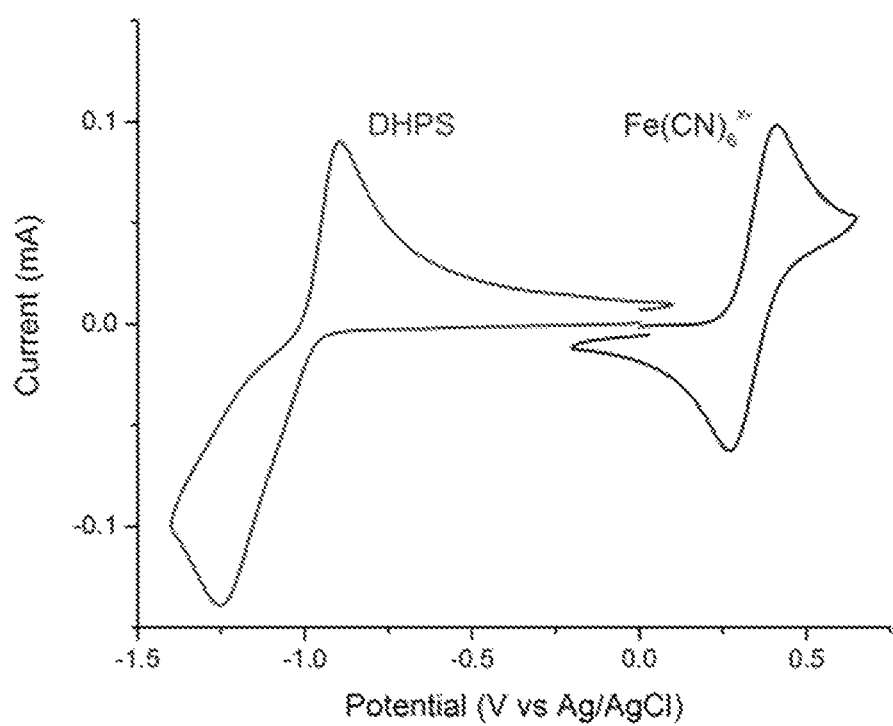
FIG. 4 shows cyclic voltammograms of 8.5 mM 7,8-dihydroxy-phenazine-2-sulfonic acid (DHPS) in 1 M NaOH and 8.5 mM ferrocyanide in 1 M NaOH.
Figure 5:
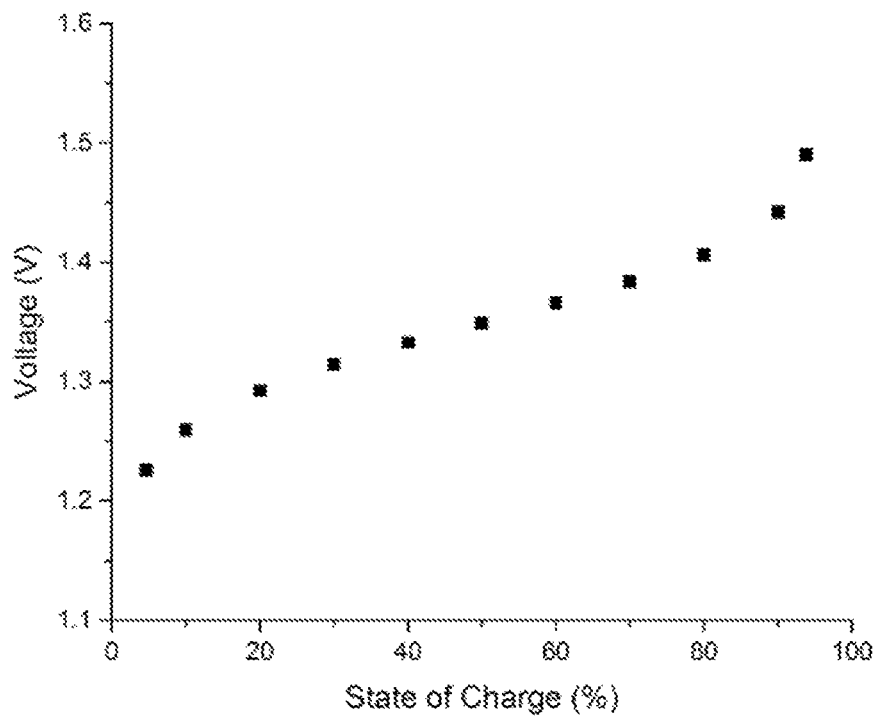
FIG. 5 is a graph of open circuit voltage vs. state of charge for the system of FIG. 3.

Analysis of DHPS by cyclic voltammetry in 1M NaOH demonstrated a highly negative redox couple at −1.08 V (vs. Ag/AgCl), as shown in FIG. 4. The cyclic voltammograms of DHPS and ferrocyanide were recorded in 1 M NaOH at a scan rate of 100 mV/sec and a concentration of 8.5 mM. Coupling of this negative potential to the ferrocyanide/ferricyanide redox couple (0.35 V) would provide a theoretical cell potential of 1.43 V. Under these conditions, the system demonstrated an open circuit voltage that exceeds 1.4 V at high state of charge (SOC), and shows a 1.35 V OCV at 50% SOC (FIG. 5). This potential exceeds all other aqueous organic flow battery systems reported to date, which, combining the high effective electron concentration resulted from high solubility, leads to high theoretical energy densities.

EXAMPLE 2

Flow Cell with Anolyte Comprising DHPS

Figure 6:
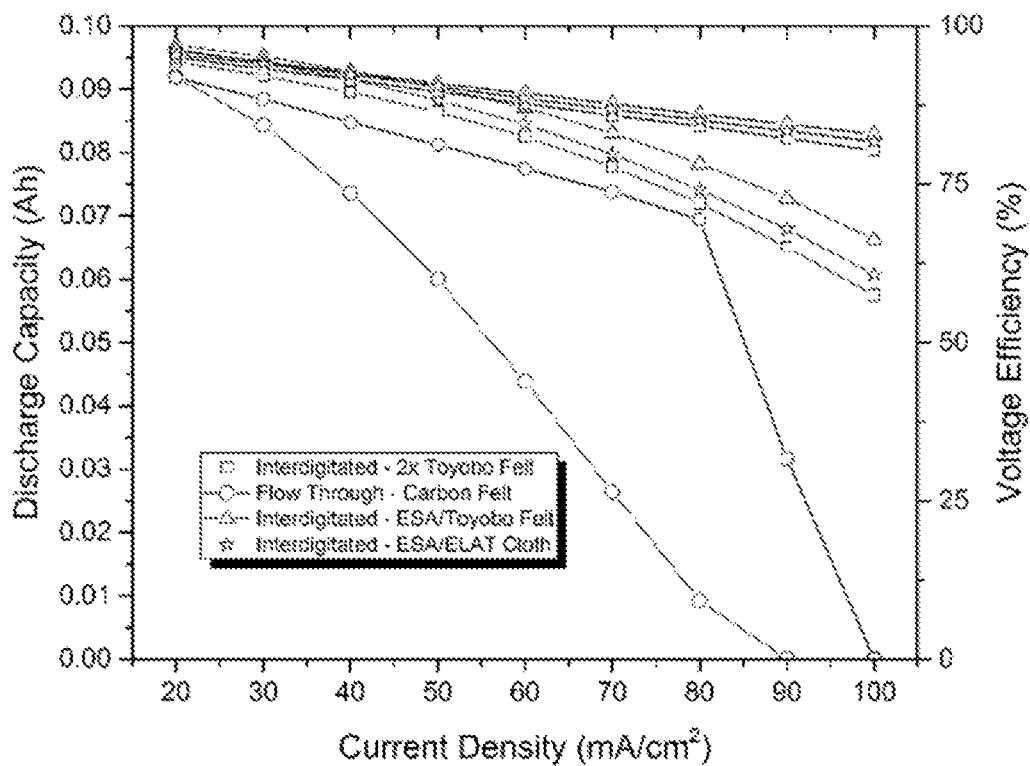
FIG. 6 is a graph of discharge capacity and voltage efficiency vs. current density for interdigitated and flow-through cells using different electrode materials.
Figure 7:
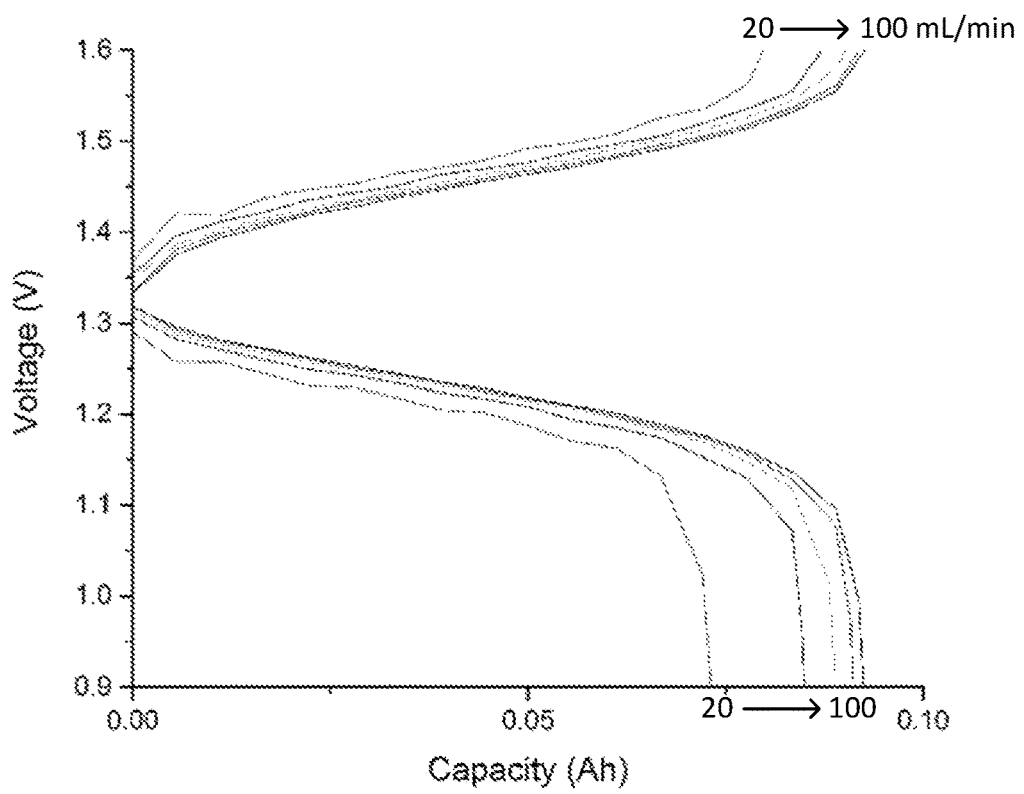
FIG. 7 is a graph of voltage vs. capacity for an interdigitated flow cell with flow rates ranging from 20 to 100 mL/minute.

Flow cell design and electrodes were evaluated. A classical flow-through design was compared to a narrow-gap interdigitated design. In each case, the anolyte was DHPS combined with 3 equivalents of NaOH and then dissolved in 1 M NaOH to yield 20 mL of a 0.1 M DHPS solution. The catholyte was 20 mL of 0.2 M $K_4Fe(CN)_6$ in 1 M NaOH. Electrode materials were selected from carbon felt, ESA carbon paper, carbon felt (Toyobo Co., Ltd., Osaka, Japan), and ELAT® carbon cloth (NuVant Systems Inc., Crown Point, Ind.). The separator was a Nafion™ N115 membrane (available from Ion Power, Inc., New Castle, Del.). An electrolyte flow rate of 100 mL/minute was used, and the voltage limits were between 1.5-1.0 V. The results are shown in FIG. 6; the best performance was obtained with the interdigitated cell with ESA/Toyobo carbon felt electrodes. An interdigitated cell with ESA/Toyobo carbon felt electrodes was used for flow rate testing at a current density of 100 mA/cm$^2$ with flow rates of 20, 40, 60, 80, and 100 mL/minute. The voltage limits were between 1.6-0.9 V. The results are shown in FIG. 7. Without wishing to be bound by a particular theory of operation, poor diffusion kinetics appear to be the primary cause of the low capacity utilization at lower flow rates.

Figure 8:
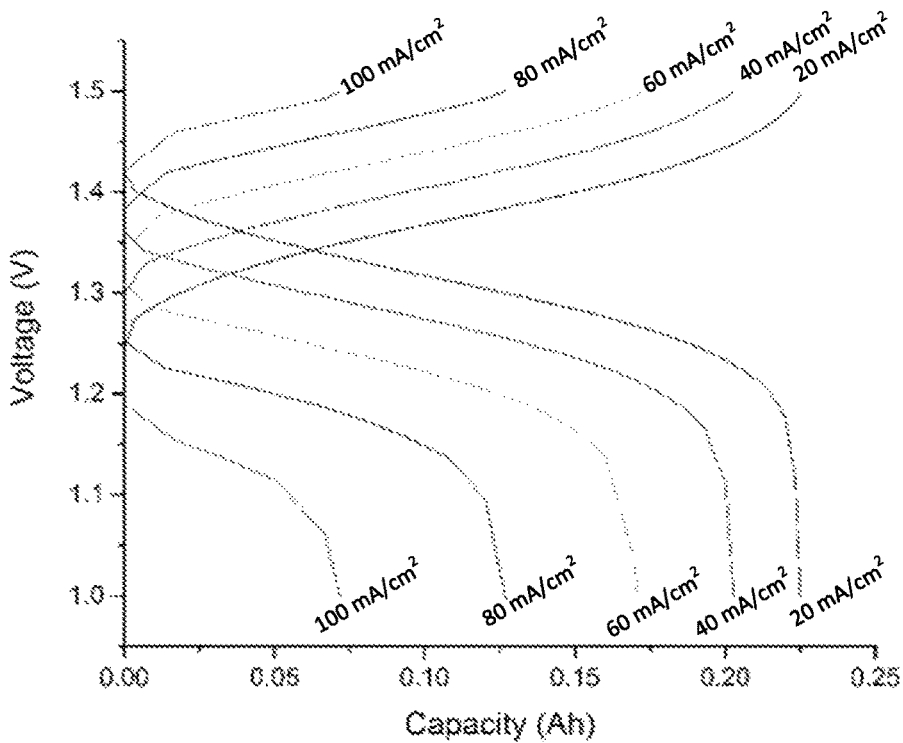
FIG. 8 is a graph of voltage vs. capacity for a flow cell including an aqueous anolyte comprising 0.1 M DHPS in 1 M NaOH and an aqueous catholyte comprising 0.2 M $K_4Fe(CN)_6$ in 1 M NaOH.
Figure 9:
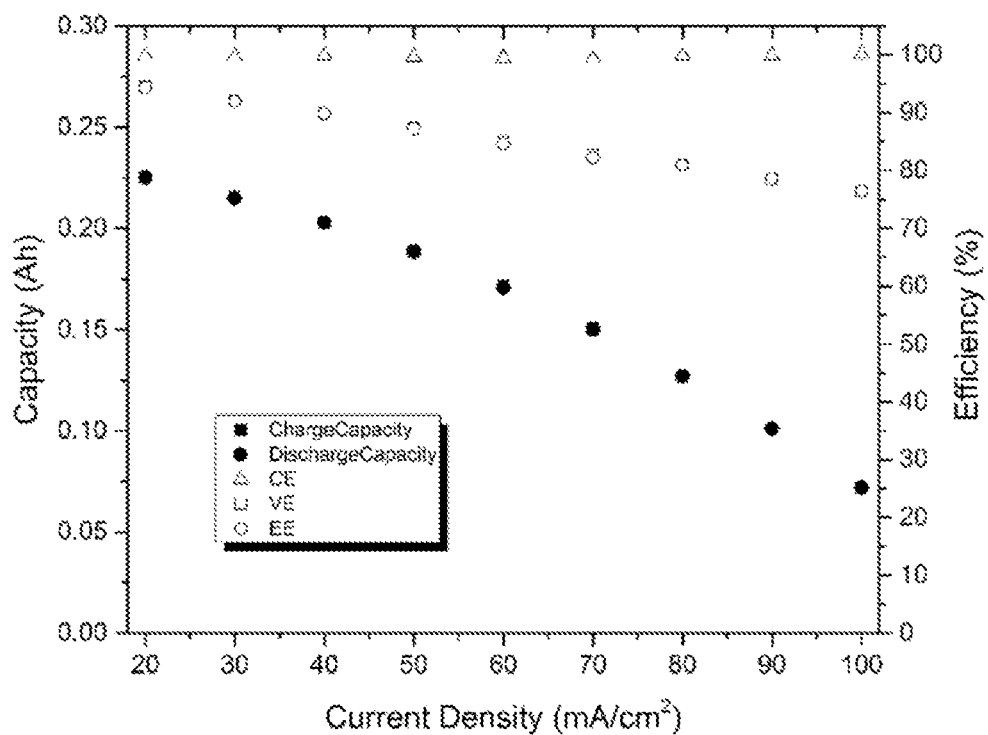
FIG. 9 shows the capacity and efficiency for the flow cell of FIG. 5 cycled at current densities from 20-100 mA/cm$^2$.
Figure 10:
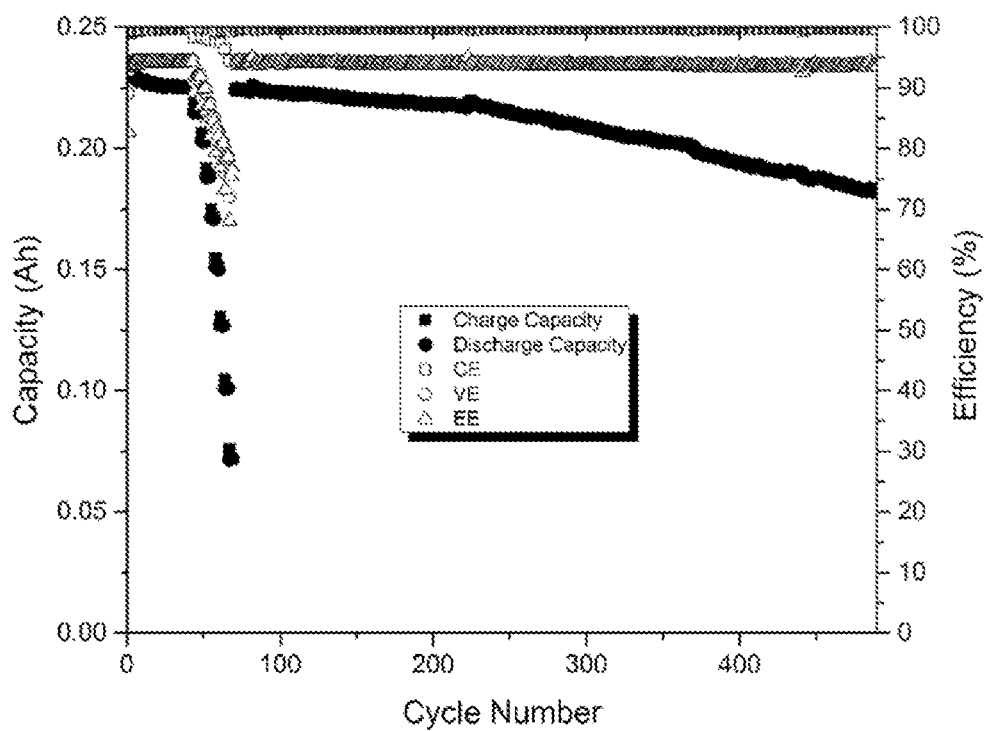
FIG. 10 shows long-term cycling of the flow cell of FIG. 5 over 500 cycles.

An interdigitated flow cell was evaluated with an aqueous anolyte comprising 0.1 M DHPS dissolved in 50 mL of 1 M NaOH and an aqueous catholyte comprising 0.2 M $K_4Fe(CN)_6$ dissolved in 50 mL of 1 M NaOH. The separator was Nafion™ N115 membrane, and the electrodes were ELAT®/ESA carbon cloth. The flow rate was 60 mL/minute. When the cell was cycled at 20 mA/cm$^2$, a material utilization of 86% was achieved (initial capacity of 0.232 Ah) with a charging voltage cutoff of 1.5 V, while the discharge plateau centered around 1.3 V (FIG. 8). A coulombic of efficiency (CE) of >99% was achieved, while a high voltage efficiency (VE) of 94% and a similar energy efficiency (EE) were also realized (FIG. 9). The discharge capacity at cycle 450 was 0.188 Ah (81% retention). At increased current densities coulombic efficiency remained >99%, however, capacity and VE both dropped: at 40 mA/cm² capacity=0.203 Ah and VE=90%, at 60 mA/cm² capacity=0.172 Ah and VE=85%, at 80 mA/cm² capacity=0.127 Ah and VE=81%, and at 100 mA/cm² capacity=0.072 Ah and VE=76%. The capacity at high current density could, however, be improved by increasing the charging voltage cutoff. Increased current density showed no lasting deleterious effects on cell performance, as returning the current density to 20 mA/cm² after altered cycling returned the cell to original performance. Long term cycling demonstrated slow capacity loss, decaying to 94% of original capacity (0.218 Ah) after 200 cycles (17 days) and 78% after 490 cycles (40 days), demonstrating longevity not only by cycle number, but also over extended time periods (FIG. 10).

Figure 11:
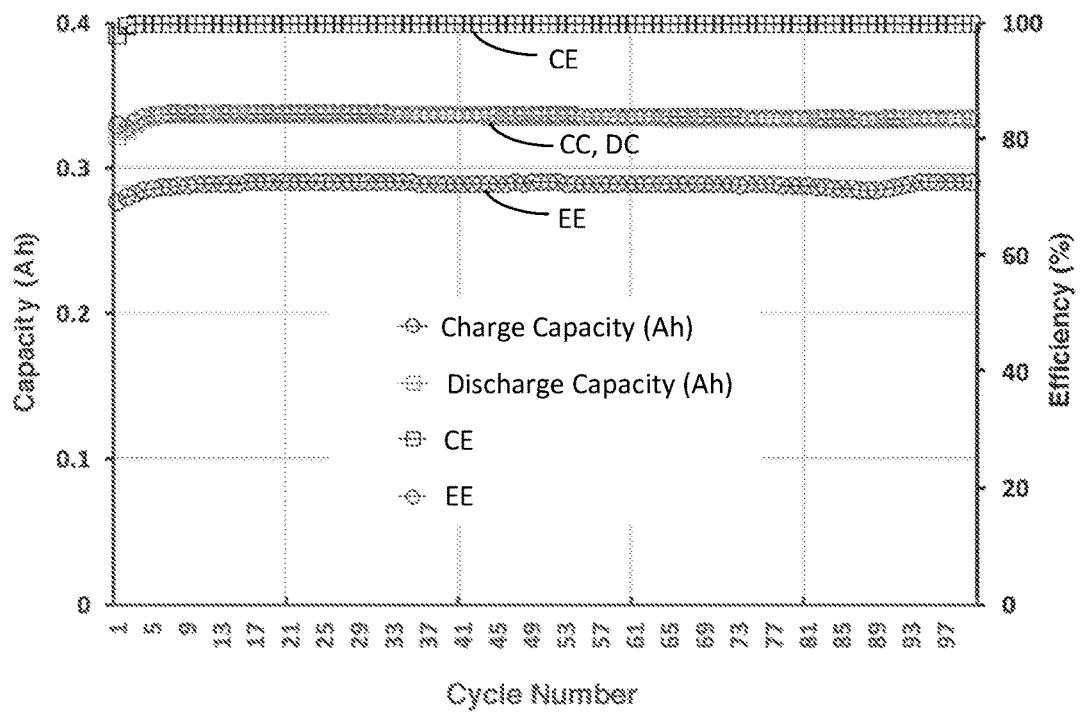
FIG. 11 shows the effects of long-term cycling on charge capacity, discharge capacity, coulombic efficiency, voltage efficiency, and energy efficiency for a cell including an anolyte comprising 1.4 M DHPS in NaOH and a catholyte comprising 0.312 M $K_4Fe(CN)_6$ and 0.312 M $K_3Fe(CN)_6$ dissolved in 45 mL of 2 M NaOH.
Figure 12:
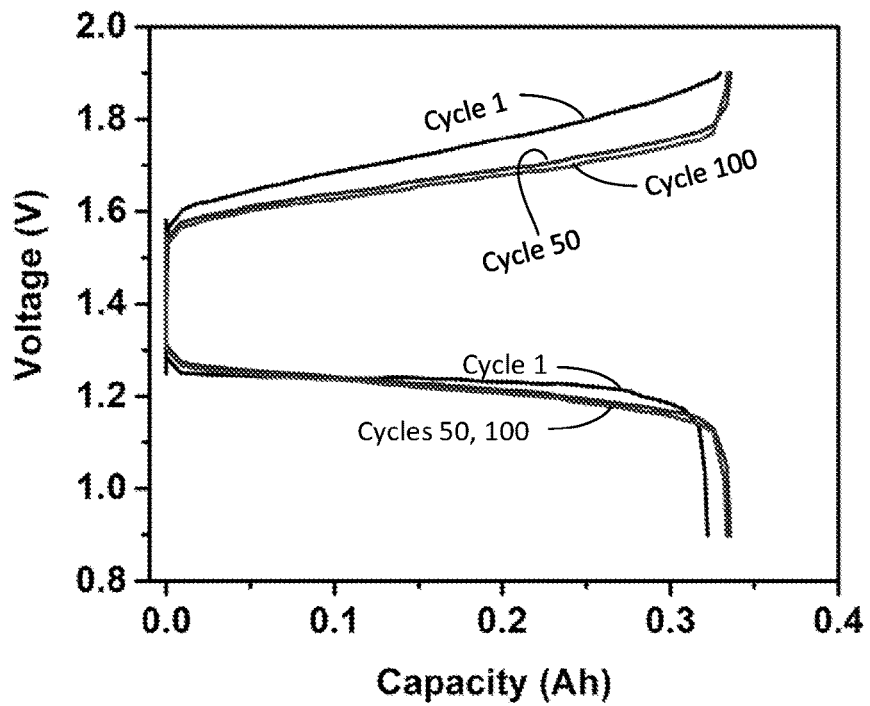
FIG. 12 shows the charge and discharge profiles of the cell of FIG. 10 at 1, 100, and 400 cycles.

A more concentrated electrolyte, 1.4 M DHPS, was evaluated. DHPS was combined with 3 equivalents of NaOH and then dissolved in 5 mL 1 M NaOH to yield a 1.4 M DHPS solution. The catholyte was 0.312 M $K_4Fe(CN)_6$ and 0.312 M $K_3Fe(CN)_6$ dissolved in 45 mL of 2 M NaOH. The separator was a Nafion™ NR212 membrane, and the electrodes were ESA/Toyobo felt. The flow rate was 100 mL/min. When the battery was cycled at 100 mA/cm², a material utilization of 88% was achieved with a coulombic efficiency of >99.5% (FIG. 11). The flow cell demonstrated excellent cycling stability without detectable capacity decay (FIG. 11). The average energy efficiency was 72% over the course of 100 cycles (FIG. 11). Charge and discharge profiles at 1, 50, and 100 cycles are shown in FIG. 12.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:
1. An aqueous electrolyte, comprising:
water; and
a phenazine derivative according to formula I or a salt thereof, where formula I is

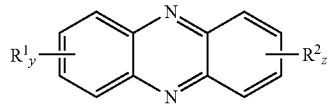

(I)

wherein each $R^1$ independently is —H, —OCH₃, —$R^aSO_3H$, —$R^aCOOH$, —$R^aSO_3M$, —$R^aCOOM$, —$R^aNR^3_3X$, —$R^aNR^3_2$, —$R^aPO(OH)_2$, —$R^aSH$, —$R^aPS(OH)_2$, —$R^a$—O—$PO(OH)_2$, —$R^a$—O—$PS(OH)_2$, —$R^a$—S—$PS(OH)_2$, or —$(OCH_2CH_2)_nOR^3$,
each $R^2$ independently is —H or —$R^aOH$, wherein at least one $R^2$ is other than hydrogen,
each $R^3$ independently is H or $C_1$-$C_5$ alkyl,
each $R^a$ independently is absent or $C_1$-$C_5$ alkyl,
M is a cation,
X is an anion,
n is an integer ≥1, and y+z=1, 2, 3, 4, 5, 6, 7, or 8, where y is 0, 1, 2, 3, or 4 and z is 1,2, 3, or 4,
wherein the aqueous electrolyte does not include any electrochemically active component other than the phenazine derivative.

2. The aqueous electrolyte of claim 1, wherein:
y is 0, 1, or 2;
z is 1 or 2; and
y+z=2, 3, or 4.

3. The aqueous electrolyte of claim 1, wherein:
each $R^1$ independently is —$SO_3H$, —COOH, or —$OCH_3$; and
each $R^2$ is —OH.

4. The aqueous electrolyte of claim 1, further comprising a base.

5. The aqueous electrolyte of claim 1, further comprising an acid.

6. The aqueous electrolyte of claim 1, wherein the electrolyte has an average pH within a range of 6.5 to 7.5, the electrolyte further comprising at least one aqueous-soluble neutral salt other than a phenazine derivative salt.

7. The aqueous electrolyte of claim 1, wherein the phenazine derivative has a structure according to formula II

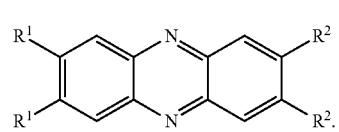

(II)

wherein each $R^1$ independently is —H, —OCH₃, —$R^aSO_3H$, —$R^aCOOH$, —$R^aSO_3M$, —$R^aCOOM$, —$R^aNR^3_3X$, —$R^aNR^3_2$, —$R^aPO(OH)_2$, —$R^aSH$, —$R^aPS(OH)_2$, —$R^a$—O—$PO(OH)_2$, —$R^a$—O—$PS(OH)_2$, —$R^a$—S—$PS(OH)_2$, or —$(OCH_2CH_2)_nOR^3$,
each $R^2$ independently is —H or —$R^aOH$, wherein at least one $R^2$ is other than hydrogen;
each $R^3$ independently is H or $C_1$-$C_5$ alkyl;
each $R^a$ independently is absent or $C_1$-$C_5$ alkyl;
M is a cation;
X is an anion; and
n is an integer ≥1.

8. The aqueous electrolyte of claim 7, wherein:
each $R^1$ independently is —H, —$SO_3H$, —COOH, or —OCH₃; and
each $R^2$ independently is —H or —OH, wherein at least one $R^2$ is —OH.

9. The aqueous electrolyte of claim 1, wherein the phenazine derivative is:

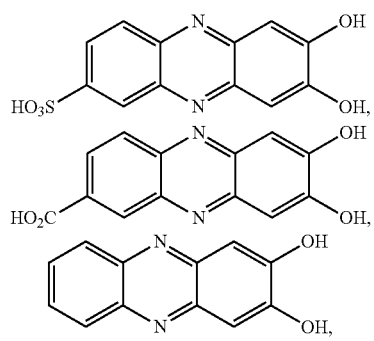

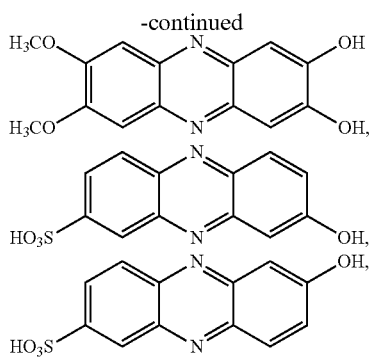

or any combination thereof.

10. The aqueous electrolyte of claim 1, wherein the aqueous electrolyte further comprises an alkali metal hydroxide.

11. The aqueous electrolyte of claim 1, wherein the phenazine derivative is

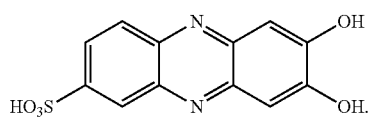 [SMILES: O=S(=O)(O)c1ccc2nc3cc(O)c(O)cc3nc2c1]

12. The aqueous electrolyte of claim 1, consisting essentially of:
 a base;
 the phenazine derivative; and
 water.

13. The aqueous electrolyte of claim 1, where the phenazine derivative is present in the electrolyte at a concentration within a range of from 0.01 M to 8 M.

14. An aqueous electrolyte system for use in a redox flow battery system, comprising:
 an aqueous anolyte comprising the aqueous electrolyte according to claim 1; and
 an aqueous catholyte comprising an electrochemically active material.

15. The aqueous electrolyte system of claim 14, wherein the aqueous catholyte further comprises a base or an acid.

16. The aqueous electrolyte system of claim 14, wherein the electrochemically active material of the aqueous catholyte comprises $K_4Fe(CN)_6$, $K_3Fe(CN)_6$, or a combination thereof.

17. The aqueous electrolyte system of claim 14, wherein:
 the aqueous anolyte comprises an alkali metal base, and or any combination thereof; and
 the aqueous catholyte comprises an alkali metal base and $K_4Fe(CN)_6$, $K_3Fe(CN)_6$, or a combination thereof.

18. The aqueous electrolyte system of claim 14, wherein:
 the aqueous anolyte comprises an alkali metal base and

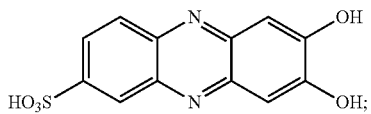

and
 the aqueous catholyte comprises the alkali metal base and $K_4Fe(CN)_6$, $K_3Fe(CN)_6$, or a combination thereof.

19. A redox flow battery system, comprising:
 the aqueous electrolyte system of claim 14; and
 a separator.

20. The redox flow battery system of claim 19, further comprising a carbon-based anode and a carbon-based cathode.

* * * * *